United States Patent
Kim et al.

(10) Patent No.: US 8,877,763 B2
(45) Date of Patent: Nov. 4, 2014

(54) SUBSTITUTED PYRIDOPYRIMIDINE COMPOUNDS AND THEIR USE AS FLT3 INHIBITORS

(71) Applicants: Genosco, Santa Fe Springs, CA (US); Oscotec, Inc., Gyeongg-Do (KR)

(72) Inventors: Hong Woo Kim, Cambridge, MA (US); Hee Kyu Lee, Gyeonggi-Do (KR); Ho-Juhn Song, Andover, MA (US); Jaekyoo Lee, North Andover, MA (US); Jong Sung Koh, Gyeonggi-Do (KR); Jung-Ho Kim, Gyeonggi-Do (KR); Se Won Kim, Gyeonggi-Do (KR); In Yong Lee, Belmont, MA (US)

(73) Assignees: Genosco, Santa Fe Springs, CA (US); Oscotec, Inc., Cheonan (KR)

( * ) Notice: Subject to any disclaimer, the term of this patent is extended or adjusted under 35 U.S.C. 154(b) by 0 days.

(21) Appl. No.: 13/841,827

(22) Filed: Mar. 15, 2013

(65) Prior Publication Data
US 2013/0274274 A1    Oct. 17, 2013

Related U.S. Application Data

(60) Provisional application No. 61/614,274, filed on Mar. 22, 2012.

(51) Int. Cl.
| | |
|---|---|
| *A01N 43/90* | (2006.01) |
| *A61K 31/519* | (2006.01) |
| *A61K 45/06* | (2006.01) |
| *C07D 471/04* | (2006.01) |
| *C07D 487/04* | (2006.01) |
| *C07D 239/00* | (2006.01) |
| *A61K 31/31* | (2006.01) |

(52) U.S. Cl.
CPC .............. *A61K 31/519* (2013.01); *A61K 45/06* (2013.01); *C07D 471/04* (2013.01); *C07D 239/00* (2013.01); *C07D 487/04* (2013.01); *A61K 31/31* (2013.01)
USPC ..................... 514/264.11; 544/279

(58) Field of Classification Search
CPC ... C07D 239/70; C07D 239/00; A61K 31/519
USPC ..................... 544/279; 514/264.11
See application file for complete search history.

(56) References Cited

U.S. PATENT DOCUMENTS

| 8,338,481 B2 * | 12/2012 | Kloog et al. | 514/546 |
| 8,404,677 B2 * | 3/2013 | Kim et al. | 514/218 |
| 2011/0269739 A1 * | 11/2011 | Kim et al. | 514/210.21 |

FOREIGN PATENT DOCUMENTS

| WO | WO-2010-019637 | 2/2010 |
| WO | WO-2011-053861 | 5/2011 |
| WO | WO 2011053861 A1 * | 5/2011 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman'S: The Pharmacological Basis of Therapeutics 1315-1403, 1315 (L.L. Brunton et al., eds., 11th ed., 2006).*
The Penguin Dictionary of Science (M.G. Clugston ed., 2009).*
P. Brown et al., 105 Blood, 812-820 (2005).*
S.J. Taylor et al., 120 Blood, 4049-4057 (2012).*
H.K. Lee et al., 123 Blood, 2209-2219 (2014).*
D. Small, 45 Seminars in Hematology, S17-S21 (2008).*
Rewcastle et al., "Tyrosine kinase inhibitors. 10. Isomeric 4-[(3-bromophenyl)amino]pyrido[d]-pyrimidines are potent ATP binding site inhibitors of the tyrosine kinase function of the epidermal growth factor receptor", J. Med. Chem., vol. 39, pp. 1823-1835 (1996).
Chen et al., "Synthesis of 8-aryl-substituted 4-(5-chloropyrido[4,3-d]pyrimidine-2-yl)morpholines as intermediates of potential PI3K inhibitors via selective Suzuki-Miyaura cross-coupling reaction", ARKIVOC, vol. 2009, Part (xi), pp. 257-267 (2009).
International Search Report and Written Opinion mailed Jul. 30, 2013, in corresponding PCT Application No. PCT/US2013/032575.

* cited by examiner

*Primary Examiner* — James O Wilson
*Assistant Examiner* — Alexander R Pagano
(74) *Attorney, Agent, or Firm* — Edwards Wildman Palmer LLP; Kongsik Kim; Mark D. Russett

(57) ABSTRACT

Compounds of Formula (I) and methods for inhibiting kinases, including spleen tyrosine kinases, are disclosed. Also disclosed are methods for treating a kinase-mediated disease or condition by administering to a subject a therapeutically effective amount of the compound of Formula (I).

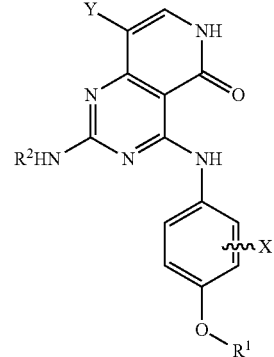

Formula I

14 Claims, No Drawings

SUBSTITUTED PYRIDOPYRIMIDINE COMPOUNDS AND THEIR USE AS FLT3 INHIBITORS

RELATED APPLICATIONS

This applications claims the benefit of and priority to U.S. Provisional Patent Application No. 61/614,274, filed Mar. 22, 2012, the contents of which are incorporated herein by reference in their entirety.

BACKGROUND OF THE INVENTION

FLT3 (FMS-like tyrosine Kinase 3, also known as Flk2) is a member of the type III receptor tyrosine kinase (RTK) family and plays an important role in the proliferation and differentiation of hematopoietic stem cells. Activating mutation or overexpression of this receptor is found in acute myeloid leukemia (AML), acute lymphocytic leukemia (ALL), mastocytosis and gastrointestinal stromal tumor (GIST). In addition to activating mutations, autocrine or paracrine ligand stimulation of overexpressed wild type FLT3 can contribute to the malignant phenotype.

The ligand for FLT3 is expressed by the marrow stromal cells and other cells and synergizes with other growth factors to stimulate proliferation of stem cells, progenitor cells, dendritic cells, and natural killer cells. FLT3 has been implicated in hematopoietic disorders which are pre-malignant disorders including myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes. Hematological malignancies include leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma. Aberrant expression of FLT3 has been documented in both adult and childhood leukemias including acute myeloid leukemia (AML), AML with trilineage myelodysplasia (AML/TMDS), acute lymphoblastic leukemia (ALL), and myelodysplastic syndrome (MDS).

The FLT3 receptor is also expressed in a large portion of dendritic cell progenitors, and stimulation of the receptor causes the proliferation and differentiation of these progenitors into dendritic cells (DC). Since dendritic cells are the main initiators of the T-cell mediated immune response, including the autoreactive immune response, FLT3 inhibition is a mechanism for down-regulating DC-mediated inflammatory and autoimmune responses. One study shows the FLT3 inhibitor CEP-701 to be effective in reducing myelin loss in experimental autoimmune encephalomyelitis (EAE), a mouse model for multiple sclerosis. A high level of the FLT3 ligand is found in the serum of patients with Langerhans cell histocytosis and systemic lupus erythematosus, which further implicates FLT3 signaling in the dysregulation of dendritic cell progenitors in those autoimmune diseases (Rolland et al., J. Immunol., 2005, 174:3067-3071).

The proto-oncogene receptor tyrosine kinase (RTK) MER (also known as MERTK, Nyk, and Tyro12) is a member of the MER/AXL/TYRO3 receptor kinase family. Within the hematopoietic lineages, MER is expressed in dendritic cells, monocytes/macrophages, NK cells, NKT cells, megakaryocytes, and platelets. However, MER is not expressed in normal lymphocytes. In studies of T-cell ALL, it was demonstrated that ectopic expression of MER contributes to the development of lymphoblastic leukemia and lymphoma. MER RNA expression has also been demonstrated in E2A-PBX1$^+$B-ALL. MER is known to activate anti-apoptotic signaling proteins, including Akt and Erk 1/2. Furthermore, a recent microarray study identified gash, a ligand for MER, as a gene which promotes survival of HEK-293 cells under conditions of serum withdrawal. Ectopic expression of MER was found in pediatric B-cell ALL Inhibition of MER prevented Erk 1/2 activation, increased the sensitivity of B-ALL cells to cytotoxic agents in vitro by promoting apoptosis, and delayed disease onset in a mouse model of leukemia. In addition, it was discovered cross-talk between the MER and mammalian target of rapamycin (mTOR) signaling pathways. MER is recently paid attention as a novel therapeutic target in ALL (Linger et al., Blood, 2009, 114(13):2678-87). Abnormal expression and activation of MER provide a survival advantage for leukemia cells. Furthermore, inhibition of MER may enhance the sensitivity of leukemia cells to cytotoxic agents.

VEGFR3 (vascular endothelial growth factor receptor 3, also known as FLT4, PCL) is a tyrosine kinase receptor of VEGFR 1, 2, 3 family for vascular endothelial growth factors (VEGF) C and D and plays an important role in lymphangiogenesis and maintenance of the lymphatic endothelium. VEGF is a signaling protein involved in the regulation of angiogenesis and vasculogenesis. It is also known that the VEGF-C/VEGFR-3 axis is expressed not only by lymphatic endothelial cells but also by a variety of human tumour cells. Activation of the VEGF-C/VEGFR-3 axis in lymphatic endothelial cells can facilitate metastasis by increasing the formation of lymphatic vessels (lymphangiogenesis) within and around tumors. The VEGF-C/VEGFR-3 axis plays a critical role in leukaemic cell proliferation, survival, and resistance to chemotherapy. Moreover, it was found that the activated VEGF-C/VEGFR-3 axis enhances cancer cell mobility and invasion capabilities, promoting cancer cell metastasis in several types of solid tumors such as gastric cancer, breast cancer, non-small cell lung cancer, cervical cancer, colorectal cancer, prostate cancer, Kaposi sarcoma, head and neck squamous cell carcinoma, endometrial carcinoma and mesothelioma (Su et al., Br. J. Cancer. 2007 96(4): 541-5)

Aurora-B (also known as serine/threonine kinase 12 and ARK2), one of Aurora family A, B, C, is a intracellular serine/threonine kinase, which is known to be directly involved in regulating the cleavage of polar spindle microtubules and is a key regulator for the onset of cytokinesis during mitosis. An important target of Aurora B is histone H3, which is a critical regulator of chromosome condensation. Aurora kinases have been strongly linked to the progression of human cancers. Overexpression of Aurora A and B is observed in many cancers such as prostate, colon, pancreas, breast and thyroid cancers. It was also found that hematologic malignant cells including those from acute myeloid leukemia (AML), acute lymphoblastic leukemia (ALL), and chronic myeloid leukemia (CML) aberrantly expressed Aurora A and B kinases (Ikezoe et al., Blood, 2006, 108:563a).

Protein kinases are attractive and proven targets for new therapeutic agents to treat a range of human diseases, with examples including Gleevec and Tarceva. The FLT-3, MER, VEGFR and Aurora-B kinase are especially attractive due to their association with numerous human cancers, particularly leukemia and lymphoma, and their roles of playing in the proliferation of these cancer cells.

WO2011053861 discloses kinase inhibitors which show inhibitory activity against multiple kinases including but not limited to FLT3 (FMS-like tyrosine Kinase).

Therefore, there remains a need to identify further compounds which have potent activity against FLT3 enzymes, higher selectivity to other kinases, and good pharmacokinetic profile to be useful to treat the FLT3 related diseases.

SUMMARY OF THE INVENTION

The present invention provides a compound of Formula I, as well as individual stereoisomers, mixture of isomers, or pharmaceutically acceptable salt thereof,

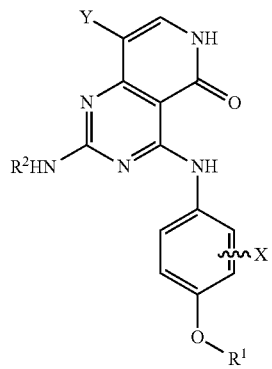

Formula (I)

wherein:
$R^1$ is aryl, arylalkyl, $C_5$-$C_6$cycloalkyl or $C_5$-$C_6$cycloalkyl methyl optionally substituted with $R^3$;
$R^3$ is independently fluoro, chloro, bromo, iodo, $C_1$-$C_6$alkyl, or $CF_3$;
X is F, Cl, Br, I, $CH_3$, or $CF_3$;
Y is chloro, bromo, iodo, $C_1$-$C_3$alkyl or phenyl;
$R^2$ is $C_3$-$C_6$cycloalkyl or $C_4$-$C_7$heterocycloalkyl, wherein the $C_3$-$C_6$cycloalkyl is optionally substituted at carbon atoms with 1 or 2 $R^4$, and wherein the $C_4$-$C_7$heterocycloalkyl has 1 or 2 heteroatoms selected from the group consisting of nitrogen, oxygen, sulfur, sulfone, or sulfoxide, and is independently substituted at carbon with $R^4$ or at nitrogen with $R^5$;
  $R^4$ is hydroxyl, hydroxyl($C_1$-$C_6$)alkyl, amino, amino($C_1$-$C_6$)alkyl, $NHC_1$-$C_3$alkyl, $N(C_1$-$C_3$alkyl)$_2$, $C_1$-$C_3$alkyl or halo;
  $R^5$ is H, $C_1$-$C_3$alkyl or $C(O)C_1$-$C_3$alkyl, wherein the $C_1$-$C_3$alkyl group is optionally substituted with 1-3 fluorine atoms;
or a pharmaceutically acceptable salt thereof.

The compounds of Formula (I) are useful for inhibiting one or more protein kinases and for treating diseases and disorders that are mediated by the protein kinases, such as cancer, autoimmune diseases, infection, cardiovascular disease, and neurodegenerative diseases. The compounds of Formula (I) are useful for inhibiting protein kinase to treat the FLT3 related diseases.

In one aspect, the present invention provides pharmaceutical compositions comprising a compound of Formula (I) and a pharmaceutically acceptable carrier. In certain embodiments, such pharmaceutical compositions are formulated for intravenous administration, subcutaneous administration, inhalation, oral administration, rectal administration, parenteral, intravitreal administration, intramuscular administration, intranasal administration, dermal administration, topical administration, optic administration, ophthalmic administration, buccal administration, tracheal administration, bronchial administration, or sublingual administration. In other embodiments, such pharmaceutical composition are formulated as tablets, pills, capsules, a liquid, an inhalant, a nasal spray solution, a suppository, a solution, a gel, an emulsion, an ointment, eye drops or ear drops.

In one aspect, the present invention provides methods for treating a cell-proliferative disease or condition, such as cancer, comprising administering to a subject in need of such treatment a therapeutically effective amount of the compound of Formula (I) or pharmaceutically acceptable salts, pharmaceutical compositions or medicaments thereof, wherein the cell proliferative disease or condition include, for example, lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer or gastrointestinal cancer. In one aspect, the present invention provides methods of inhibiting growth of cancer cells with the compound of Formula (I) or a pharmaceutically acceptable salt thereof.

In another aspect, the present invention provides methods for treating a protein kinase-mediated disease or condition comprising administering to a subject in need of such treatment a therapeutically effective amount of the compound of Formula (I) or a pharmaceutically acceptable salt, a pharmaceutical composition or a medicament thereof. The protein kinase includes, but is not limited to, FLT3 (including mutant forms such as FLT3 D835Y), MER, VEGF1 and Aurora-B.

In certain embodiments, protein kinase-mediated diseases or conditions are inflammatory diseases or conditions, respiratory diseases or autoimmune diseases or conditions, such as asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, rheumatoid arthritis, multiple sclerosis, cancer, breast cancer, HIV associated diseases or lupus.

In another aspect, the present invention provides methods for inhibiting protein kinases, comprising administering to a subject in need thereof, a therapeutically effective amount of the compound of Formula (I) or a pharmaceutically acceptable salt or pharmaceutical composition thereof. The protein kinase includes, but are not limited to, FLT3, MER, VEGF1 and Aurora-B as well as mutant form such as FLT3-D835Y.

In another aspect, the present invention provides methods for treating a cardiovascular disease by administering to a subject a therapeutically effective amount of the compound of Formula (I) or a pharmaceutically acceptable salt. Such a cardiovascular disease affects the heart or blood vessels and includes, for example, atherosclerosis, arrhythmia, angina, myocardial ischemia, myocardial infarction, cardiac or vascular aneurysm, vasculitis, stroke, peripheral obstructive arteriopathy of a limb, an organ, or a tissue, reperfusion injury following ischemia of an organ or a tissue, endotoxic, surgical, or traumatic shock, hypertension, valvular heart disease, heart failure, abnormal blood pressure, vasoconstriction, vascular abnormality, or inflammation.

In another aspect, the present invention provides methods of treating a kinase-mediated disease or condition by administering to a subject a therapeutically effective amount of the compound of Formula (I) or a pharmaceutically acceptable salt in combination with a second therapeutic agent.

In the above methods for using the compound of the invention, the compound of Formula (I) or a pharmaceutically acceptable salt is administered to a system comprising cells or tissues. In certain embodiments, the compound of Formula (I), a pharmaceutically acceptable salt, a pharmaceutical composition or a medicament thereof is administered to a human or animal subject.

The present invention also relates to compositions comprising these compounds, methods of making these compounds, methods of inhibiting enzyme activity, particularly FLT3 and its mutant form FLT3 D835Y kinase activity, through use of these compounds, and method of treating disease or disease symptoms in a mammal, particularly where inhibition of the kinase activity, can affect disease outcome.

DETAILED DESCRIPTION OF THE INVENTION

The present invention provides a group of 4-phenylamino-pyrido[4,3,-d]pyrimidin-5-one derivatives and pharmaceutically acceptable salts thereof that are useful for inhibiting one or more protein kinases and for treating diseases and disorders that are mediated by the protein kinases, for example, cell proliferative disease. The present invention also provides methods of synthesizing and administering the 4-phenylamino-pyrido[4,3,-d]pyrimidin-5-one derivatives. The present invention provides pharmaceutical formulations comprising at least one of the compounds together with a pharmaceutically acceptable carrier, diluent or excipient therefor. The invention also provides useful intermediates generated during syntheses of 4-phenylamino-pyrido[4,3,-d]pyrimidin-5-one derivative compounds.

Disclosed herein is a novel class of compounds having Formula (I), and pharmaceutically acceptable salts, N-oxide derivatives, prodrug derivatives, protected derivatives, individual isomers and mixture of isomers thereof for inhibiting protein kinases.

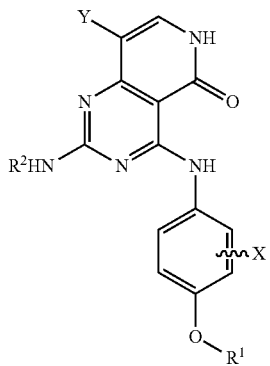

Formula (I)

wherein:
$R^1$ is aryl, arylalkyl, $C_5$-$C_6$cycloalkyl or $C_5$-$C_6$cycloalkyl methyl optionally substituted with $R^3$;
$R^3$ is independently fluoro, chloro, bromo, iodo, $C_1$-$C_6$alkyl, or $CF_3$;
X is F, Cl, Br, I, $CH_3$, or $CF_3$;
Y is chloro, bromo, iodo, $C_1$-$C_3$alkyl or phenyl;

$R^2$ is $C_3$-$C_6$cycloalkyl or $C_4$-$C_7$heterocycloalkyl, wherein the $C_3$-$C_6$cycloalkyl is optionally substituted at carbon atoms with 1 or 2 $R^4$, and wherein the $C_4$-$C_7$heterocycloalkyl has 1 or 2 heteroatoms selected from the group consisting of nitrogen, oxygen, sulfur, sulfone, or sulfoxide, and is independently substituted at carbon with $R^4$ or at nitrogen with $R^5$;
$R^4$ is hydroxyl, hydroxyl($C_1$-$C_6$)alkyl, amino, amino($C_1$-$C_6$)alkyl, $NHC_1$-$C_3$alkyl, $N(C_1$-$C_3$alkyl$)_2$, $C_1$-$C_3$alkyl or halo;
$R^5$ is H, $C_1$-$C_3$alkyl or $C(O)C_1$-$C_3$alkyl, wherein the $C_1$-$C_3$alkyl group is optionally substituted with 1-3 fluorine atoms;
or a pharmaceutically acceptable salt thereof.

In certain embodiments, $R^1$ represents phenyl, benzyl, cyclopentyl, cyclohexyl, cyclopentyl methyl, or cyclohexyl methyl.

In certain embodiments, $R^3$ represents fluorine, chlorine, $CH_3$, or isopropyl.

In certain embodiments, $R^3$ represents H, methyl or F.

In one embodiment, Y represents chloro, bromo, iodo, methyl or phenyl. In further embodiments, Y represents chloro or bromo.

In certain embodiments, $R^5$ represents methyl. In certain embodiments, $R^2$ represents pyrrolidinyl, or piperidinyl. In certain embodiments, $R^2$ represents N-methylpyrrolidinyl or N-methyl piperidinyl.

In certain embodiments, $R^6$ represents hydroxyl, hydroxyl ($C_1$-$C_6$)alkyl, amino, amino($C_1$-$C_6$)alkyl, $NHC_1$-$C_3$alkyl, $N(C_1$-$C_3$alkyl$)_2$, $C_1$-$C_3$alkyl or halo. In certain embodiments, $R^6$ represents hydroxyl, amino, or N-methyl amino.

The term "alkyl," used alone or as part of a larger moiety such as "arylalkyl" or "cycloalkyl" refers to a straight or branched hydrocarbon radical having from 1 to 15 carbon atoms or from 1-8 carbon atoms (unless stated otherwise) and includes, for example, methyl, ethyl, n-propyl, iso-propyl, n-butyl, sec-butyl, isobutyl, tert-butyl, n-pentyl, iso-pentyl, n-hexyl and the like. An alkyl can be unsubstituted or substituted with one or more suitable substituents.

The term "cycloalkyl" refers to a monocyclic or polycyclic hydrocarbon ring group and includes, for example, cyclopropyl, cycloheptyl, cyclooctyl, cyclodecyl, cyclobutyl, adamantyl, norpinanyl, decalinyl, norbornyl, cyclohexyl, cyclopentyl, and the like. A cycloalkyl group can be unsubstituted or substituted with one or more suitable substituents.

The term "hetero" refers to the replacement of at least one carbon atom member in a ring system with at least one heteroatom such as nitrogen, sulfur, and oxygen.

The term "heterocycloalkyl" means a non-aromatic monocyclic or polycyclic ring comprising carbon and hydrogen atoms and at least one heteroatom, preferably, 1 to 4 heteroatoms selected from nitrogen, sulfur, oxygen, sulfone, or sulfoxide. A heterocycloalkyl group can have one or more carbon-carbon double bonds or carbon-heteroatom double bonds in the ring group as long as the ring group is not rendered aromatic by their presence.

Examples of heterocycloalkyl groups include azetidinyl, aziridinyl, pyrrolidinyl, piperidinyl, piperazinyl, homopiperazinyl, morpholino, thiomorpholino, tetrahydrofuranyl, tetrahydrothiofuranyl, tetrahydropyranyl, pyranyl, and the like. A heterocycloalkyl group can be unsubstituted or substituted with one or more suitable substituents.

As used herein, the term "halo" includes fluoro, chloro, bromo, and iodo.

As used herein, the term "alkoxy" refers to the alkyl groups above bound through oxygen, examples of which include methoxy, ethoxy, iso-propoxy, tert-butoxy, and the like. In addition, alkoxy also refers to polyethers such as —O—(CH$_2$)$_2$—O—CH$_3$, and the like. An alkoxy can be unsubstituted or substituted with one or more suitable substituents.

As used herein, the term "aryl" refers to unsubstituted or substituted aromatic monocyclic or polycyclic groups and includes, for example, phenyl and naphthyl. The term "aryl" also includes a phenyl ring fused to a non-aromatic carbocyclic or heterocyclic ring. The term "aryl" may be interchangeably used with "aryl ring," aromatic group," and "aromatic ring." Heteroaryl groups have 4 to 14 atoms, 1 to 9 of which are independently selected from the group consisting of oxygen, sulfur and nitrogen. Heteroaryl groups have 1-3 heteroatoms in a 5-8 membered aromatic group. An aryl or heteroaryl can be a mono- or bicyclic aromatic group. Typical aryl and heteroaryl groups include, for example, phenyl, quinolinyl, indazoyl, indolyl, dihydrobenzodioxynyl, 3-chlorophenyl, 2,6-dibromophenyl, pyridyl, pyrimidinyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, pyrrole, pyrazole, imidazole, thiazole, and the like. An aryl or heteroaryl can be unsubstituted or substituted with one or more suitable substituents.

As used herein, the term "haloalkyl" refers to any alkyl radical having one or more hydrogen atoms replaced by a halogen atom. Examples of haloalkyl include —CF$_3$, —CFH$_2$, —CF$_2$H, and the like.

As used herein, the term "hydroxyl" or "hydroxy" refers to —OH.

As used herein, the term "amino" refers to —NH$_2$.

As used herein, the term "hydroxyalkyl" refers to any hydroxyl derivative of alkyl radical. The term "hydroxyalkyl" includes any alkyl radical having one or more hydrogen atoms replaced by a hydroxy group.

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

As described above, certain groups can be unsubstituted or substituted with one or more suitable substituents by other than hydrogen at one or more available positions, typically 1, 2, 3, 4 or 5 positions, by one or more suitable groups (which may be the same or different). Certain groups, when substituted, are substituted with 1, 2, 3 or 4 independently selected substituents. Suitable substituents include halo, alkyl, haloalkyl, aryl, hydroxy, alkoxy, hydroxyalkyl, amino, and the like.

As used herein, the term "kinase" refers to a list of protein kinases, including but not limited to FLT3, MER, Aurora-B, VEGF1, and their mutant forms such as FLT3 D835Y. Kinase assays containing the kinases described herein are commercially available for biochemically profiling kinase inhibitors for their selectivity. In certain embodiments, a kinase is a mammalian kinase, such as a human kinase.

As used herein, the term "dermatological disorder" refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, and urticaria.

As used herein, the term "respiratory disease" refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation,
child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

As used herein, the term "cancer" refers to an abnormal growth of cells which tend to proliferate in an uncontrolled way and, in some cases, to metastasize. The types of cancer include, but is not limited to, solid tumors, such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

As used herein, the term "inflammatory disorders" refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function, which may be partial or complete, temporary or permanent. Inflammation takes many forms and includes, but is not limited to, inflammation that is one or more of the following, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporarl arteritis); joints (arthritis: crystalline, osteo-, psoriatic, reactive, rheumatoid, Reiter's); gastrointestinal tract; skin (dermatitis); or multiple organs and tissues (systemic lupus erythematosus).

As used herein, the term "cardiovascular disease" refers to diseases affecting the heart or blood vessels or both, including but not limited to atherosclerosis, arrhythmia, angina, myocardial ischemia, myocardial infarction, cardiac or vascular aneurysm, vasculitis, stroke, peripheral obstructive arteriopathy of a limb, an organ, or a tissue, reperfusion injury following ischemia of an organ or a tissue, endotoxic, surgical, or traumatic shock, hypertension, valvular heart disease, heart failure, abnormal blood pressure, vasoconstriction, vascular abnormality, or inflammation.

As used herein, the term "inhibitor" refers to a compound which inhibits one or more kinases described herein. For example, the term "FLT3 inhibitor" refers to a compound which inhibits the FLT3 receptor or reduces the signaling effect.

As used herein, the term "pharmaceutically acceptable" refers to a material, such as a carrier or diluent, which does not abrogate the biological activity or properties of the compounds described herein. Such materials are administered to an individual without causing undesirable biological effects or interacting in a deleterious manner with any of the components of the composition in which it is contained.

As used herein, the term "pharmaceutically acceptable salt" refers to a formulation of a compound that does not cause significant irritation to an organism to which it is administered and does not abrogate the biological activity and properties of the compounds described herein.

As used herein, the term "pharmaceutical combination" means a product that results from the mixing or combining of more than one active ingredient.

As used herein, the term "pharmaceutical composition" refers to a mixture of a compound described herein with other chemical components, such as carriers, stabilizers, diluents, dispersing agents, suspending agents, thickening agents, and/or excipients.

As used herein, the term "prodrug" refers to an agent that is converted into an active or "parent" drug in vivo.

As used herein, the term "protein kinase-mediated disease" or a "disorder or disease or condition mediated by inappropriate protein kinase activity" refers to any disease state mediated or modulated by protein kinases described herein. Such disease states include, but are not limited to, asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, bullous disorders, collagenoses, contact dermatitis eczema, Kawasaki Disease, rosacea, Sjogren-Larsso Syndrome, rheumatoid arthritis, multiple sclerosis, inflammatory bowel syndrome, HIV, lupus, lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer, gastrointestinal cancer, Alzheimer's disease, Parkinson's disease, osteoporosis, osteopenia, osteomalacia, osteofibrosis, Paget's disease, diabetes, blood vessel proliferative disorders, ocular diseases, cardiovascular disease, restenosis, fibrosis, atherosclerosis, arrhythmia, angina, myocardial ischemia, myocardial infarction, cardiac or vascular aneurysm, vasculitis, stroke, peripheral obstructive arteriopathy, reperfusion injury following ischemia of an organ or a tissue, endotoxic, surgical or traumatic shock, hypertension, valvular heart disease, heart failure, abnormal blood pressure, vasoconstriction, vascular abnormality, transplant rejection and infectious diseases including viral and fungal infections.

As used herein, the term "kinase-mediated disease" or "kinase-mediated disease" or a "disorder or disease or condition mediated by inappropriate kinase activity" refers to any disease state mediated or modulated by a kinase mechanism. For example "FLT3-mediated disease" refers to any disease state mediated or modulated by FLT3 mechanisms. Such FLT3-mediated disease states include, but are not limited to, leukemia including acute myeloid leukemia (AML), acute lymphoid leukemia (ALL), inflammatory, respiratory diseases, autoimmune diseases, multiple sclerosis, other myeloproliferative disorders cancer or a condition associated with aberrantly increased levels of FLT3 kinase As used herein, the term "MER-mediated disease" or a "disorder or disease or condition mediated by inappropriate MER activity" refers to any disease state mediated or modulated by MER kinase mechanisms. Such disease states include, but are not limited to, AML, ALL, solid tumors, other proliferative disorders, or a condition associated with aberrantly increased levels of MER kinase.

As used herein, the term "VEGFR3-mediated disease" or a "disorder or disease or condition mediated by inappropriate VEGFR3 activity" refers to any disease state mediated or modulated by VEGFR3 kinase mechanisms. Such disease states include, but are not limited to AML, ALL, solid tumors, other proliferative disorders, or a condition associated with aberrantly increased levels of VEGFR3 kinase.

As used herein, the term "Aurora B-mediated disease" or a "disorder or disease or condition mediated by inappropriate Aurora B activity" refers to any disease state mediated or modulated by Aurora B kinase mechanisms. Such disease states include, but are not limited to, AML, ALL, solid tumors, other proliferative disorders, or a condition associated with aberrantly increased levels of Aurora B kinase.

As used herein, the term "therapeutically effective amount" refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "solvate" refers to a complex of variable stoichiometry formed by a solute (in this invention, a compound of Formula (I) or a pharmaceutically acceptable salt thereof) and a solvent. Such solvents for the purpose of the invention may not interfere with the biological activity of the solute. Non-limiting examples of suitable solvents include water, acetone, methanol, ethanol and acetic acid. Preferably the solvent used is a pharmaceutically acceptable solvent. Non-limiting examples of suitable pharmaceutically acceptable solvents include water, ethanol and acetic acid.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "administration" or "administering" of the subject compound refers to providing a compound of the invention and/or prodrugs thereof to a subject in need of treatment.

As used herein, the term "carrier" refers to chemical compounds or agents that facilitate the incorporation of a compound described herein into cells or tissues.

As used herein, the term "acceptable" with respect to a formulation, composition or ingredient, as used herein, means having no persistent detrimental effect on the general health of the subject being treated.

As used herein, the term "diluent" refers to chemical compounds that are used to dilute a compound described herein prior to delivery. Diluents can also be used to stabilize compounds described herein.

As used herein, the term "effective amount" or "therapeutically effective amount" refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system.

For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. By way of example only, a therapeutically effective amount of a compound of the invention may be in the range of e.g., about 0.01 mg/kg/day to about 100 mg/kg/day, or from about 0.1 mg/kg/day to about 10 mg/kg/day.

I. Human Protein Kinases

Protein kinases play a central role in the regulation of a wide variety of cellular processes and maintaining control over cellular function. Protein kinases catalyze and regulate the process of phosphorylation, whereby the kinases covalently attach phosphate groups to proteins or lipid targets in response to a variety of extracellular signals. Examples of such stimuli include hormones, neurotransmitters, growth and differentiation factors, cell cycle events, environmental stresses and nutritional stresses. An extracellular stimulus may affect one or more cellular responses related to cell growth, migration, differentiation, secretion of hormones, activation of transcription factors, muscle contraction, glucose metabolism, control of protein synthesis, and regulation of the cell cycle.

The compounds of the present invention were screened against the kinase panel and inhibited the activity of at least one kinase on the panel. Examples of kinases include, but are not limited to FLT3, MER, Aurora-B, VEGF1, and mutant forms such as FLT3 D835Y kinases. As such, the compounds and compositions of the invention are useful for treating diseases or disorders in which such kinases contribute to the pathology and/or symptomology of a disease or disorder associated with such kinases. Such diseases or disorders include, but are not limited to, pancreatic cancer, papillary thyroid carcinoma, ovarian carcinoma, human adenoid cystic carcinoma, non-small cell lung cancer, secretory breast carcinoma, congenital fibrosarcoma, congenital mesoblastic nephroma, acute myelogenous leukemia, psoriasis, metastasis, cancer-related pain and neuroblastoma, autoimmune diseases, inflammatory diseases, bone diseases, metabolic diseases, neurological and neurodegenerative diseases, cancer, cardiovascular diseases, respiratory diseases, allergies and asthma, Alzheimer's disease, and hormone related diseases, benign and malignant proliferative disorders, diseases resulting from inappropriate activation of the immune system, diseases resulting from inappropriate activation of the nervous system, allograft rejection, graft vs. host disease, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, diabetes mellitus, diabetic angiopathy, retinopathy of prematurity, infantile hemangiomas, non-small cell lung, bladder and head and neck cancers, prostate cancer, breast cancer, ovarian cancer, gastric and pancreatic cancer, psoriasis, fibrosis, atherosclerosis, restenosis, autoimmune disease, allergy, respiratory diseases, asthma, transplantation rejection, inflammation, thrombosis, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, Alzheimer's disease, Parkinson's disease, disorders or conditions related to nerve damage and axon degeneration subsequent to a brain or spinal cord injury, acute or chronic cancer, ocular diseases, viral infections, heart disease, lung or pulmonary diseases or kidney or renal diseases and bronchitis.

The compounds described herein are inhibitors of kinase activity and have therapeutic benefit in the treatment of disorders associated with inappropriate kinase activity, in particular in the treatment and prevention of disease states mediated by kinase. Therefore, the present invention provides methods of regulating, and in particular inhibiting, signal transduction cascades in which a kinase plays a role. The method generally involves administering to a subject or contacting a cell expressing the kinase with an effective amount of a compound described herein, prodrug, or an acceptable salt, hydrate, solvate, N-oxide and/or composition thereof, to regulate or inhibit the signal transduction cascade. The methods are also used to regulate, and in particular inhibit, downstream processes or cellular responses elicited by activation of the particular kinase signal transduction cascade. The methods are also practiced in in vitro contexts or in in vivo contexts as a therapeutic approach towards the treatment or prevention of diseases characterized by, caused by or associated with activation of the kinase-dependent signal transduction cascade.

2. Pharmaceutical Compositions

For the therapeutic uses of compounds provided herein, including compounds of Formula (I), or pharmaceutically acceptable salts, solvates, N-oxides, prodrugs and isomers thereof, such compounds are administered in therapeutically effective amounts either alone or as part of a pharmaceutical composition. Accordingly, provided herein are pharmaceutical compositions, which comprise at least one compound provided herein, including at least one compound of Formula (I), pharmaceutically acceptable salts and/or solvates thereof, and one or more pharmaceutically acceptable carriers, diluents, adjuvant or excipients. In addition, such compounds and compositions are administered singly or in combination with one or more additional therapeutic agents.

The methods of administration of such compounds and compositions include, but are not limited to, intravenous administration, inhalation, oral administration, rectal administration, parenteral, intravitreal administration, subcutaneous administration, intramuscular administration, intranasal administration, dermal administration, topical administration, ophthalmic administration, buccal administration, tracheal administration, bronchial administration, sublingual administration or otic administration. Compounds provided herein are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like.

The therapeutically effective amount will vary depending on, among others, the disease indicated, the severity of the disease, the age and relative health of the subject, the potency of the compound administered, the mode of administration and the treatment desired. The required dosage will also vary depending on the mode of administration, the particular condition to be treated and the effect desired.

Pharmaceutically acceptable salt forms include pharmaceutically acceptable acidic/anionic or basic/cationic salts. Pharmaceutically acceptable acidic/anionic salts include, acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid addition salt is formed by reaction of the free base form a compound of Formula (I) with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

The free acid or free base forms of the compounds of the invention may be prepared from the corresponding base addition salt or acid addition salt from, respectively. For example a compound of the invention in an acid addition salt form may be converted to the corresponding free base by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Prodrug derivatives of the compounds of the invention may be prepared by methods known to those of ordinary skill in the art (e.g., for further details see Saulnier et al., (1994), Bioorganic and Medicinal Chemistry Letters, Vol. 4, 1985; the entire teachings of which are incorporated herein by reference).

Protected derivatives of the compounds of the invention may be made by means known to those of ordinary skill in the art. A detailed description of techniques applicable to the creation of protecting groups and their removal can be found in T. W. Greene, "Protecting Groups in Organic Chemistry," 3rd edition, John Wiley and Sons, Inc., 1999, the entire teachings of which are incorporated herein by reference.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981, the entire teachings of which are incorporated herein by reference.

Suitable pharmaceutically acceptable carriers, diluents, adjuvant or excipients for use in the pharmaceutical compositions of the invention include tablets (coated tablets) made of for example collidone or shellac, gum Arabic, talc, titanium dioxide or sugar, capsules (gelatin), solutions (aqueous or aqueous-ethanolic solution), syrups containing the active substances, emulsions or inhalable powders (of various saccharides such as lactose or glucose, salts and mixture of these excipients with one another) and aerosols (propellant-containing or -free inhale solutions).

Excipients which may be used include, for example, water, pharmaceutically acceptable organic solvents such as paraffins (e.g., petroleum fractions), vegetable oils (e.g. groundnut or sesame oil), mono- or polyfunctional alcohols (e.g., ethanol or glycerol), carriers such as natural mineral powders (e.g., kaoline, clays, talc, chalk), synthetic mineral powders (e.g., highly dispersed silicic acid and silicates), sugars (e.g., cane sugar, lactose and glucose), emulsifiers (e.g., lignin, spent sulphite liquors, methylcellulose, starch and polyvinylpyrrolidone) and lubricants (e.g., magnesium stearate, talc, stearic acid and sodium lauryl sulphate).

Compounds of Formula (I) are made by processes described herein and in the Examples. In certain embodiments, compounds of Formula (I) are made by: (a) optionally converting a compound of the invention into a pharmaceutically acceptable salt; (c) optionally converting a salt form of a compound of the invention to a non-salt form; (d) optionally converting an unoxidized form of a compound of the invention into a pharmaceutically acceptable N-oxide; (e) optionally resolving an individual isomer of a compound of the invention from a mixture of isomers; (f) optionally converting a non-derivatized compound of the invention into a pharmaceutically acceptable prodrug derivative; and (g) optionally converting a prodrug derivative of a compound of the invention to its non-derivatized form.

The teachings of all patents, published applications and references cited herein are incorporated by reference in their entirety.

EXAMPLES

The present invention is further exemplified by the following examples that illustrate the preparation of compounds of Formula (I) according to the invention. The examples are for illustrative purpose only and are not intended, nor should they be construed as limiting the invention in any manner. Those skilled in the art will appreciate that variations and modifications can be made without changing the scope of the invention.

Liquid chromatography-mass spectrometry (LC-MS) Method:
 1. Samples are run on Agilent Technologies 6120 MSD system with a Zorbax Eclipse XDB-C18 (3.5µ) reverse phase column (4.6×50 mm) run at room temperature with flow rate of 1.5 mL/minute.
 2. The mobile phase uses solvent A (water/0.1% formic acid) and solvent B (acetonitrile/0.1% formic acid): 95%/5% to 0%/100% (A/B) for 5 minute.
 3. The mass spectra (m/z) were recorded using electrospray ionization (ESI).
 4. Ionization data was rounded to the nearest integer.

The invention provides a method for preparing a compound of Formula (I) starting from the compound a (Scheme 1), which can be prepared as described in PCT Publication No. WO2011053861.

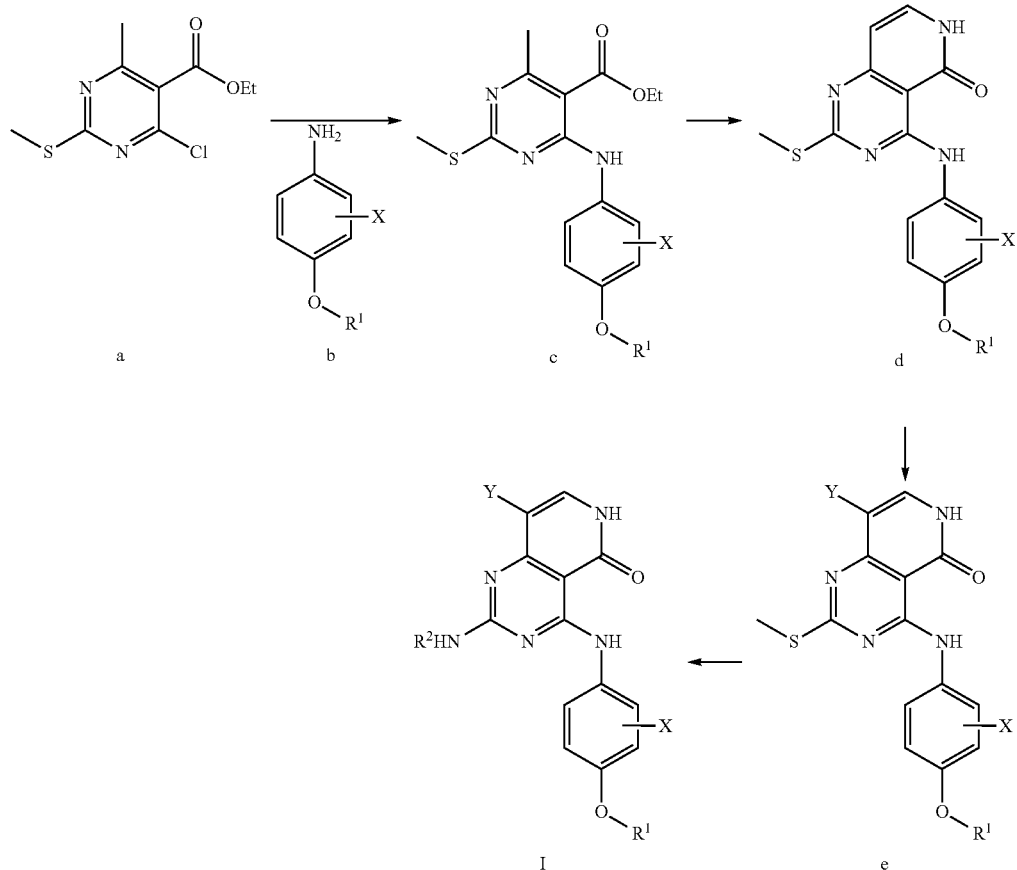

Scheme 1.

Compound c was prepared by reacting the compound a with the compound b under acidic conditions (see Scheme 1). Then the compound c was treated with N,N-dimethylformamide dimethylacetal (DMF DMA) followed by ammonia in ethanol to yield the compound d. The preparation of the compound e was accomplished by using of N-halosuccinimide. The compound e was oxidized with inorganic oxidant forming the corresponding sulfone. The sulfone compound underwent a coupling reaction with various amine $R^2NH_2$ in the presence of organic base to provide the compound of Formula (I). The detailed synthetic reaction condition of the compound (238) is described below.

Ethyl 4-(4-(3-fluorophenoxy)phenyl)amino)-6-methyl-2-(methylthio)pyrimidine-5-carboxylate (238c); A 40 mL reaction vial was charged with a (1.85 g, 7.52 mmol), and 4-(3-fluorophenoxy)aniline (1.65 g, 8.10 mmol) in 10 mL acetic acid. After being stirred at 100° C. for 2 hours, volatiles were removed under reduced pressure yielding the brown residue. The residue was dissolved in methylene chloride and then washed with saturated aqueous sodium bicarbonate solution. The separated organic layer was dried over sodium sulfate and then concentrated to give (239c) as a brown residue. The resulting crude product was used to next step without purification.

Ethyl 4-methyl-2-(methylthio)-6-(4-phenoxyphenylamino)pyrimidine-5-carboxylate (222c); (222c) was prepared from 4-phenoxybenzenamine by the method of example (238c).

4-((4-(3-fluorophenoxy)phenyl)amino)-2-(methylthio) pyrido[4,3-d]pyrimidin -5(6H)-one (238d); The crude residue (238c) was dissolved in DMF (5 mL). To this, was added N,N-dimethylformamide dimethyl acetal (DMF/DMA, 15 mmol, 1.93 mL) at room temperature. The reaction mixture was stirred at 130° C. for 16 hours. The volatiles were removed under reduced pressure yielding the brown residue. The residue was dissolved in methylene chloride and washed with water. The separated organic layer was condensed to afford brown oil. The resulted oily residue was dissolved in hot ethanol in a 40 mL reaction vial. To this, was added 30% aq. ammonium hydroxide (2 mL) solution, and then the vial was capped well and stirred at 100° C. for 4 h. The reaction was cooled down to room temperature to form solid precipitates. The resulted solids were collected by filtration and washed with ethanol yielding 1.58 g of 238d as orange solids (53% for the three steps).

8-Bromo-4-((4-(3-fluorophenoxy)phenyl)amino)-2-(methylthio)pyrido[4,3-d]pyrimidin-5(6H)-one (238e); A 40 mL reaction vial was charged with 238d, (1.00 g, 2.53 mmol) in 15 mL of DMF. The mixture was gently heated until it became a clear solution, and allowed to cool down to room temperature. To the mixture was added N-bromosuccinimide (NBS, 498 mg, 2.80 mmol) and stirred for 1 h at rt. The solvent was removed under reduced pressure yielding the orange solid. The resulting solids were collected by filtration and washed acetonitrile to provide 1.04 g (87%) of the desired product 238e.

8-bromo-4-((4-(3-fluorophenoxy)phenyl)amino)-2-((1-methylpiperidin-4-yl)amino)pyrido[4,3-d]pyrimidin-5(6H)-one (238); A 40 mL reaction vial was charged with 238e (0.90 g, 1.90 mmol) in 15 mL DMF. The clear solution was cooled to −10° C. To this, was added m-CPBA (1.48 g, 6.00 mmol) at −10° C. The reaction was allowed to warm up to room temperature, and then stirred for additional 30 min at RT. To the mixture was added TEA (0.83 mL, 6.00 mmol) and 1-methylpiperidin-4-amine (685 mg, 6.00 mmol), and then it was stirred at room temperature for 1 hour with monitoring the reaction by LC-MS. The solvent was removed under reduced pressure yielding light brown oily residue. The residue was dissolved in methylene chloride and washed with saturated aqueous sodium bicarbonate solution. The separated organic layer was dried over sodium sulfate, and then concentrated under reduced pressure to yield a solid. The solid was dissolved in a minimum amount of methylene chloride and treated with excess of n-hexanes yielding pale yellow solids. The resulted solids were collected by filtration, rinsed with n-hexanes and then dried in the air yielding a pale yellow solid. The solid was dissolved in the mixture of DCM and methanol. To the clear solution was added 4N HCl in dioxane (12.0 mL), then it was stirred at room temperature for 6 hours. The solvent was removed under reduced pressure yielding the desired product (238, 90% yield).

8-Bromo-2-(1-methylpiperidin-4-ylamino)-4-(4-phenoxyphenylamino)pyrido[4,3-d]pyrimidin-5(6H)-one hydrochloride (226); Prepared from (226c) by the method of (238). MS (ESI) m/z 521 [M+1]$^+$, 523 [M+3]$^+$. $^1$H NMR (400M Hz, CDCl$_3$) δ (ppm) 11.62(s, 0.7H), 11.42(s, 0.3H), 11.09(b, 1H), 7.70-7.79(m, 2H), 7.56(m, 1H), 7.32-7.39(m, 2H), 7.02-7.14 (m, 5H), 5.79(d, J=7.32 Hz, 0.7H), 5.43(d, J=7.04 Hz, 0.3H), 3.88(m, 0.3H), 3.75(m, 0.7H), 2.90(m, 2H), 2.01-2.37(m, 7H), 1.66(m, 2H).

TABLE 1

| No | Structure | MS (ESI+) m/z |
|---|---|---|
| 221 | [structure] | 535 |
| 222 | [structure] | 521 |
| 223 | [structure] | 513 |
| 224 | [structure] | 541 |

TABLE 1-continued

| No | Structure | MS (ESI+) m/z |
|---|---|---|
| 225 | 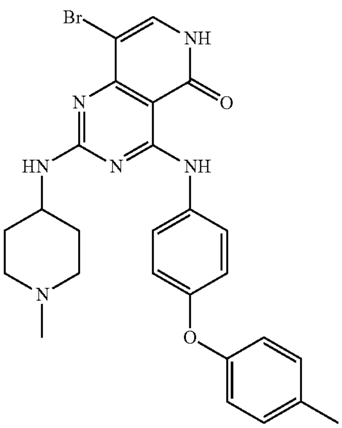 [SMILES: Cc1ccc(Oc2ccc(Nc3nc(NC4CCN(C)CC4)nc4c(Br)c[nH]c(=O)c34)cc2)cc1] | 535 |
| 226 | 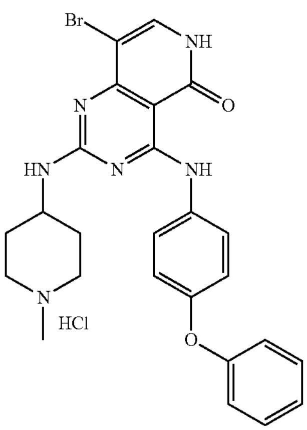 [SMILES: CN1CCC(Nc2nc(Nc3ccc(Oc4ccccc4)cc3)c3c(=O)[nH]cc(Br)c3n2)CC1 ; Cl] | 521 |
| 227 | 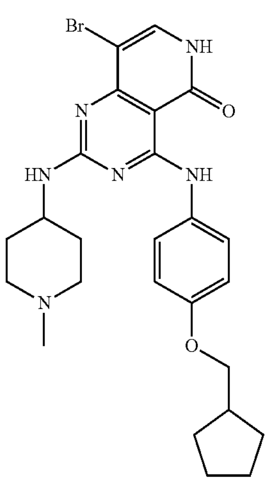 [SMILES: CN1CCC(Nc2nc(Nc3ccc(OCC4CCCC4)cc3)c3c(=O)[nH]cc(Br)c3n2)CC1] | 527 |
| 228 | | 527 |
| 229 | | 483 |
| 230 | | 563 |

TABLE 1-continued

| No | Structure | MS (ESI+) m/z |
|---|---|---|
| 231 | 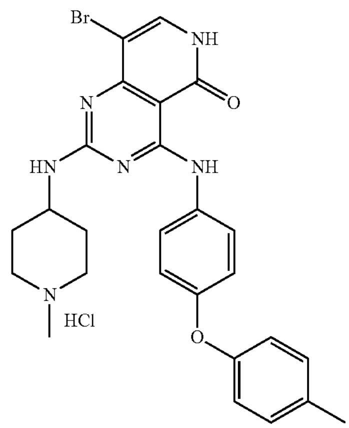 [SMILES: Cc1ccc(Oc2ccc(Nc3nc(NC4CCN(C)CC4)nc4c(Br)c[nH]c(=O)c34)cc2)cc1 ; Cl] | 535 |
| 232 | 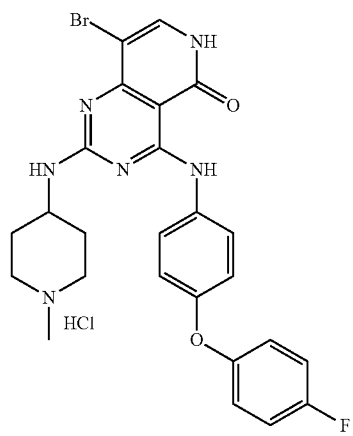 [SMILES: CN1CCC(Nc2nc(Nc3ccc(Oc4ccc(F)cc4)cc3)c3c(=O)[nH]cc(Br)c3n2)CC1 ; Cl] | 539 |
| 233 | 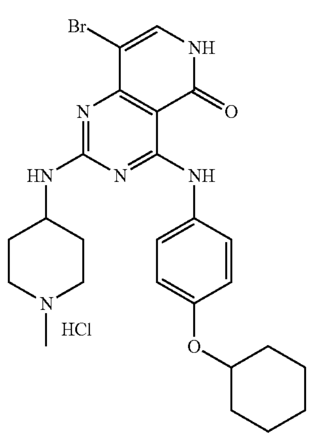 [SMILES: CN1CCC(Nc2nc(Nc3ccc(OC4CCCCC4)cc3)c3c(=O)[nH]cc(Br)c3n2)CC1 ; Cl] | 527 |
| 234 | | 535 |
| 235 | | 527 |
| 236 | | 563 |

TABLE 1-continued

| No | Structure | MS (ESI+) m/z |
|---|---|---|
| 237 | [structure: 8-bromo-pyrido-pyrimidinone with 2-(1-methylpiperidin-4-yl)amino·HCl and 4-[(4-cyclopentyloxyphenyl)amino]] | 513 |
| 238 | [structure: 8-bromo-pyrido-pyrimidinone with 2-(1-methylpiperidin-4-yl)amino·HCl and 4-[(4-(3-fluorophenoxy)phenyl)amino]] | 539 |
| 239 | [structure: 8-bromo-pyrido-pyrimidinone with 2-(1-methylpiperidin-4-yl)amino·HCl and 4-[(4-(2-methylphenoxy)phenyl)amino]] | 535 |
| 240 | [structure: 8-bromo-pyrido-pyrimidinone with 2-(1-methylpiperidin-4-yl)amino and 4-[(4-(3-fluorophenoxy)phenyl)amino]] | 539 |
| 241 | [structure: 8-bromo-pyrido-pyrimidinone with 2-(1-methylpiperidin-4-yl)amino·HCl and 4-[(4-(3,4-difluorophenoxy)phenyl)amino]] | 557 |
| 242 | [structure: 8-bromo-pyrido-pyrimidinone with 2-(1-methylpiperidin-4-yl)amino·HCl and 4-[(4-(4-chlorophenoxy)phenyl)amino]] | 555 |

TABLE 1-continued

| No | Structure | MS (ESI+) m/z |
|---|---|---|
| 243 | 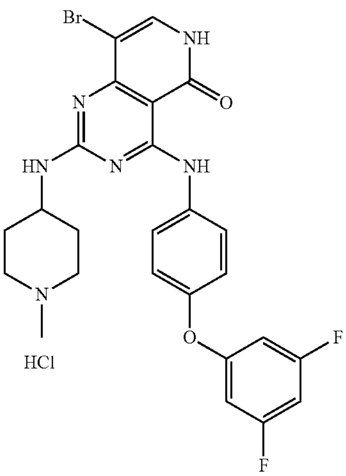 [SMILES: CN1CCC(Nc2nc(Nc3ccc(Oc4cc(F)cc(F)c4)cc3)c3c(=O)[nH]cc(Br)c3n2)CC1 ; Cl] | 557 |
| 244 | 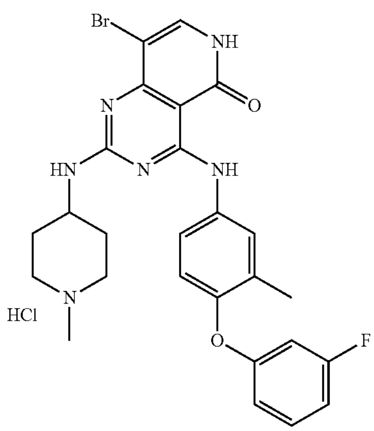 [SMILES: Cl ; Cc1cc(Nc2nc(NC3CCN(C)CC3)nc3c(Br)c[nH]c(=O)c23)ccc1Oc1cccc(F)c1] | 553 |
| 245 | 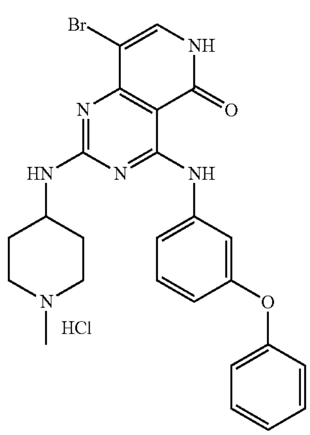 [SMILES: CN1CCC(Nc2nc(Nc3cccc(Oc4ccccc4)c3)c3c(=O)[nH]cc(Br)c3n2)CC1 ; Cl] | 521 |
| 246 | | 521 |
| 247 | | 539 |
| 248 | | 535 |

TABLE 1-continued

| No | Structure | MS (ESI+) m/z |
|---|---|---|
| 249 | (structure) | 557 |
| 250 | (structure) | 549 |
| 251 | (structure) | 535 |
| 252 | (structure) | 589 |

Table 1 shows the structures of compounds of Formula (I). Certain compounds of Formula (I) are named as follows: 4-((4-(benzyloxy)phenyl)amino)-8-bromo-2-((1-methylpiperidin-4-yl)amino)pyrido[4,3-d]pyrimidin-5(6H)-one; 8-bromo-2-((1-methylpiperidin-4-yl)amino)-4-((4-phenoxyphenyl)amino)pyrido[4,3-d]pyrimidin-5(6H)-one; 8-bromo-4-((4-(cyclopentyloxy)phenyl)amino)-2-((1-methylpiperidin-4-yl)amino)pyrido[4,3-d]pyrimidin-5(6H)-one; 8-bromo-4-((4-(cyclohexylmethoxy)phenyl)amino)-2-((1-methylpiperidin-4-yl)amino)pyrido[4,3-d]pyrimidin-5(6H)-one; 8-bromo-2-((1-methylpiperidin-4-yl)amino)-4-((4-(p-tolyloxy)phenyl)amino)pyrido[4,3-d]pyrimidin-5(6H)-one; 8-bromo-2-((1-methylpiperidin-4-yl)amino)-4-((4-phenoxyphenyl)amino) pyrido[4,3-d]pyrimidin-5(6H)-one hydrochloride; 8-bromo-4-((4-(cyclopentylmethoxy)phenyl)amino)-2-((1-methylpiperidin-4-yl)amino)pyrido[4,3-d]pyrimidin-5(6H)-one; 8-bromo-4-((4-(cyclohexyloxy)phenyl)amino)-2-((1-methylpiperidin-4-yl)amino)pyrido[4,3-d]pyrimidin-5(6H)-one; 8-chloro-4-((4-(cyclohexyloxy)phenyl)amino)-2-((1-methylpiperidin-4-yl)amino)pyrido[4,3-d]pyrimidin-5(6H)-one; 8-bromo-4-((4-(4-isopropylphenoxy)phenyl)amino)-2-((1-methylpiperidin-4-yl)amino)pyrido[4,3-d]pyrimidin-5(6H)-one; 8-bromo-2-((1-methylpiperidin-4-yl)amino)-4-((4-(p-tolyloxy)phenyl)amino)pyrido[4,3-d]pyrimidin-5(6H)-one hydrochloride; 8-bromo-4-((4-(4-fluorophenoxy)phenyl)amino)-2-((1-methylpiperidin-4-yl)amino)pyrido[4,3-d]pyrimidin-5(6H)-one hydrochloride; 8-bromo-4-((4-(cyclohexyloxy)phenyl)amino)-2-((1-methylpiperidin-4-yl)amino) pyrido[4,3-d]pyrimidin-5(6H)-one hydrochloride; 4-((4-(benzyloxy)phenyl)amino)-8-bromo-2-((1-methylpiperidin-4-yl)amino) pyrido[4,3-d]pyrimidin-5(6H)-one; 8-bromo-4-((4-(cyclopentylmethoxy)phenyl)amino)-2-((1-methylpiperidin-4-yl)amino)pyrido[4,3-d]pyrimidin-5(6H)-one; 8-bromo-4-((4-(4-isopropylphenoxy)phenyl)amino)-2-((1-methylpiperidin-4-yl)amino)pyrido[4,3-d]pyrimidin-5 (6H)-one hydrochloride; 8-bromo-4-((4-(cyclopentyloxy) phenyl)amino)-2-((1-methylpiperidin-4-yl)amino) pyrido[4,3-d]pyrimidin-5(6H)-one hydrochloride; 8-bromo-4-((4-(3-fluorophenoxy)phenyl)amino)-2-((1-methylpiperidin-4-yl)amino)pyrido[4,3-d]pyrimidin-5(6H)-one hydrochloride; 8-bromo-2-((1-methylpiperidin-4-yl)amino)-4-((4-(o-tolyloxy)phenyl)amino)pyrido[4,3-d]pyrimidin-5(6H)-one hydrochloride; 8-bromo-4-((4-(3-fluorophenoxy)phenyl)

amino)-2-((1-methylpiperidin-4-yl)amino) pyrido[4,3-d]pyrimidin-5(6H)-one; 8-bromo-4-((4-(3-fluorophenoxy)phenyl)amino)-2-((1-methylpiperidin-4-yl)amino)pyrido[4,3-d]pyrimidin-5(6H)-one; 8-bromo-4-((4-(3,4-difluorophenoxy)phenyl)amino)-2-((1-methylpiperidin-4-yl)amino)pyrido[4,3-d]pyrimidin-5(6H)-one hydrochloride; 8-bromo-4-((4-(4-chlorophenoxy)phenyl)amino)-2-((1-methylpiperidin-4-yl)amino)pyrido[4,3-d]pyrimidin-5(6H)-one hydrochloride; 8-bromo-4-((4-(3,5-difluorophenoxy)phenyl)amino)-2-((1-methylpiperidin-4-yl)amino)pyrido[4,3-d]pyrimidin-5(6H)-one hydrochloride; 8-bromo-4-((4-(3-fluorophenoxy)-3-methylphenyl)amino)-2-((1-methylpiperidin-4-yl)amino)pyrido[4,3-d]pyrimidin-5(6H)-one hydrochloride; 8-bromo-2-((1-methylpiperidin-4-yl)amino)-4-((3-phenoxyphenyl)amino)pyrido[4,3-d]pyrimidin-5(6H)-one hydrochloride; 8-bromo-2-((1-methylpiperidin-4-yl)amino)-4-((3-phenoxyphenyl)amino)pyrido[4,3-d]pyrimidin-5(6H)-one; 8-bromo-4-((3-fluoro-4-phenoxyphenyl)amino)-2-((1-methylpiperidin-4-yl)amino)pyrido[4,3-d]pyrimidin-5(6H)-one hydrochloride; 8-bromo-4-((3-methyl-4-phenoxyphenyl)amino)-2-((1-methylpiperidin-4-yl)amino)pyrido[4,3-d]pyrimidin-5(6H)-one hydrochloride; 8-bromo-4-((3-fluoro-4-(3-fluorophenoxy)phenyl)amino)-2-((1-methylpiperidin-4-yl)amino)pyrido[4,3-d]pyrimidin-5(6H)-one hydrochloride; and 8-bromo-2-(methyl(1-methylpiperidin-4-yl)amino)-4-((4-phenoxyphenyl)amino)pyrido[4,3-d]pyrimidin-5(6H)-one hydrochloride, 8-bromo-2-(1-isopropylpiperidin-4-ylamino)-4-(4-phenoxyphenylamino)pyrido[4,3-d]pyrimidin-5(6H)-one, 8-bromo-2-(1-ethylpiperidin-4-ylamino)-4-(4-phenoxyphenylamino)pyrido[4,3-d]pyrimidin-5(6H)-one, 8-bromo-4-(4-phenoxyphenylamino)-2-(1-(2,2,2-trifluoroethyl)piperidin-4-ylamino)pyrido[4,3-d]pyrimidin-5(6H)-one.

Biological Assays

1. Kinase Inhibition Assay

Compounds of the present invention were assayed to measure their capacity to inhibit kinases which include, but are not limited to, FLT3 and JAK2.

FLT3 is a member of the type III receptor tyrosine kinase (RTK) family. The ligand for FLT3 is expressed by the marrow stromal cells and other cells and synergizes with other growth factors to stimulate proliferation of stem cells, progenitor cells, dendritic cells, and natural killer cells. FLT3 has been implicated in hematopoietic disorders which are pre-malignant disorders including myeloproliferative disorders, such as AML and ALL.

JAK2 has been implicated in signaling by members of the type II cytokine receptor family (e.g., interferon receptors), the GM-CSF receptor family (IL-3R, IL-5R and GM-CSF-R), the gp130 receptor family (e.g. IL-6R), and the single chain receptors (e.g. Epo-R, Tpo-R, GH-R, PRL-R). JAK2 gene fusions with the TEL(ETV6) (TEL-JAK2) and PCM1 genes have been found in leukemia patients. Further, mutations in JAK2 have been implicated in polycythemia vera, essential thrombocythemia, and other myeloproliferative disorders. This mutation, a change of valine to phenylalanine at the 617 position, rendered hematopoietic cells more sensitive to growth factors such as erythropoietin and thrombopoietin.

Methods

Inhibition of Enzymatic FLT3 and JAK2 Kinase Activity

Compounds of the invention were initially diluted to 10 mM in 100% DMSO (CALBIOCHEM™) for storage and made into kinase buffer solution to create a compound concentration ranging from 1 uM and 10 uM. Serial dilutions of compounds of the invention were dispensed into a 96-well plate (GREINER BIOSCIENCES™) at 6 µL each. Truncated human FLT3 wildtype, mutant D835Y, and JAK2 (CARNA BIOSCIENCES™) were diluted in kinase buffer and added to the compound solutions and pre-incubated for 30 minutes at room temperature. Next, ATP (TEKNOVAT™) and substrate solution (suggested manufacture substrates of PerkinElmer™, for example, Ulight™-TK peptide for FLT3 wildtype and mutant D835Y and Ulight™-JAK1 for JAK2 (PERKINELMER™) was added (12 uL each) to the wells containing the compound solution and enzyme. The reaction mixture was incubated for 1 hour. Following the incubation, the stop solution made with EDTA, water, and Lance detection buffer (PERKINELMER™) was added (12 µL each) to stop phosphorylation. Following the addition of the stop solution and 5 minutes of shaking, the detection solution containing the Europium-labeled antibody (suggested manufacture substrates of PerkinElmer™, for example, PT66 for FLT3 and JAK2), water, and Lance detection buffer was added (12 µL each) to the reaction mixture and incubated again for 50 minutes. Substrate phosphorylation was a function of the 665 nm emission measured following the addition of the detection solution and 50 minutes of incubation.

Results

Compounds of Formula (I) exhibited useful pharmacological properties. As used herein, an way to describe potency of inhibitory activity (nM)) is a value of inhibitory activity at 50% ($IC_{50}$) as shown in Table 2. Reference compounds, AC220 (Quizartinib, Ambit), PKC412 (Midostaurin, Novartis) and staurosporine (pan-kinase inhibitor) were used for FLT3 to judge inhibitory activity of compounds of Formula (I). A reference compound, staurosporine, a pan-kinase inhibitor, was independently used for JAK2 to judge selectivity and inhibitory activity of compounds of Formula (I).

For example, the compound 238 of Formula (I), namely, 8-bromo-4-(4-(3-fluorophenoxy)phenylamino)-2-(1-methylpiperidin-4-ylamino)pyrido[4,3-d]pyrimidin-5(6H)-one hydrochloride, showed strong inhibition of kinase activity of FLT3 wildtype and mutant D835Y which is the most frequent mutant occurred in kinase domain of FLT3 found in AML patients. Its potency in biochemical assay is superior to that of clinically developing FLT3 inhibitors, AC220 and PKC412. Moreover, it displays great selectivity against its JAK2 kinase, which is superior to the reference PKC412. Table 2 illustrates the IC50 value of FLT3 and JAK2 by the representative compounds of Formula (I). As shown in Table 2, reference compounds, staurosporine and PKC-412, are multi-potent, suggesting there is no selectivity across kinases whereas compounds of the present invention show better potency and better selectivity than reference compounds. Furthermore, the compounds of the present invention also show better selectivity than those indicated by asterisk and described in Prior Art of WO2011053861 and PCT/US2010/056583. As shown in Table 2, compounds *8 and *136 show multi-kinase inhibitory activity similar to PKC-412. PKC-412 is also widely known antagonists of the vascular endothelial growth factor receptor (VEGFR) and the epidermal growth factor receptor (EGFR). Taken together, these data suggest that the compounds of the present invention significantly improve selectivity compared to previously-reported compounds, as well as inhibitory potency in FLT3 wildtype and D835Y mutant compared to known the FLT3 inhibitors, AC220 and PKC-412.

The compounds *8 and *136 described in WO2011053861 showed multiple inhibitory activities against various tested kinases including JAK2. In particular they showed no drug exposure in rat after oral administration of 10 mg/kg, suggesting that they were not absorbed in gut or were eliminated extremely fast from body.

Table 2 illustrates the biochemical inhibition of FLT3 and JAK2 by the representative compounds of Formula (I).

| Compound ID | FLT3 wildtype | JAK2 | FLT3-D835Y |
|---|---|---|---|
| PKC-412 | 15.4 | 116 | 24.2 |
| Staurosporine | 0.2 | 0.9 | 0.3 |
| *8 | 0.2 | 12.7 | 1.0 |
| *136 | 0.1 | 3.9 | 0.3 |
| *203 | 0.2 | 391 | 18.5 |
| 246 | 0.1 | 260 | 1.7 |
| 221 | 0.1 | 290 | 0.4 |
| 241 | 1.6 | 1,050 | 0.6 |

| Compound ID | FLT3 wildtype | JAK2 | FLT3-D835Y |
|---|---|---|---|
| 223 | 0.6 | 153 | 0.3 |
| 225 | 0.3 | 1521 | 1.6 |
| 226 | 1.2 | 281 | 0.2 |
| 228 | 0.1 | 129 | 0.6 |
| 233 | 0.1 | 173 | 0.3 |
| 240 | 1.2 | 599 | 1.3 |
| 238 | 1.4 | 845 | 0.4 |

*three compounds no 8, 136 and 203 were described in WO2011053861 and PCT/US2010/056583.

All data are listed in $IC_{50}$ value.

2. Cell Viability Assay: Inhibition of FLT3-ITD-Positive Cells

Compounds of the invention are tested for their effects on inhibition of FLT3-ITD (Internal Tandem Duplication) in human acute leukemia cell line (MV4-11). FLT3 is primarily expressed in immature hematopoietic progenitor as well as in mature myeloid cells. It belongs to type III receptor tyrosine kinase (RTK) family including KIT, FMS, and PDGFR. It is activated by binding to FL, which leads to increased kinase activity and activation of downstream signaling pathway including STATS, Ras, and PI3Kinase.

The FLT3-ITD mutations in the juxtamembrane domain are the most frequently observed molecular defect in acute myelogenous leukemia (AML). The FLT3-ITD induces ligand-independent dimerization, autophosphorylation and constitutive activation, and is able to transform hematopoietic cells. Clinically, FLT3-ITD is known to increased leukocytosis, increased blast count, increased relapse rate, decreased disease-free survival, and poor overall survival. Therefore, FLT3-ITD is an attractive molecular target for AML therapy.

Methods

Compounds of the invention were tested for cell viability effect on MV4-11 cells. For cell viability assay, MV4-11 cells expressing human FLT3-ITD were obtained from the American Type Culture Collection (ATCC, Manassas, Va.). This cell line was maintained with an Roswell Park Memorial Institute (RPMI) medium (HyClone™) containing 10 bovine calf serum (BCS; Hyclone™) supplemented iron. The MV4-11 cells were seeded at $2 \times 10^4$ cells in 96-well culture plates, and serially diluted compound was then added. After a 72 hour incubation period at 37° C., cell viability was measured using the ATPLite 1 step assay (Perkin-Elmer™) that is based on the quantification of ATP from viable cells. CellTiter Aqueous assay (Promega™) was also performed in parallel as an orthogonal assay. $IC_{50}$ values were calculated using nonlinear regression and defined as the concentration needed for a 50 reduction in luminescence or absorbance treated versus untreated control cells (Prism™ Software).

Results

The $IC_{50}$ inhibition data of the representative compounds of Formula (I) are shown in Table 3. Compounds of Formula (I) exhibited an inhibition of less than 10 nM at $IC_{50}$ concentration. Specially, the compound 237, 8-bromo-4-(4-(cyclopentyloxy)phenylamino)-2-(1-methylpiperidin-4-ylamino)pyrido[4,3-d]pyrimidin-5(6H)-one hydrochloride, exhibited an inhibition level greater than those exhibited by reference PKC-412 in FLT3 ITD induced MV4-11 cancer cell line. Such strong anti-tumor activity suggests that the compounds of the present invention are better therapeutic value than the reference and the compound 203 indicated by asterisks described in the Prior Art (PCT file no: PCT/US2010/056583).

TABLE 3

Cell Viability by FLT3-ITD Induced Cancer Cell Line by the representative compounds of Formula (I).

| Compound ID | MV4-11 cell ($IC_{50}$) | Compound ID | MV4-11 cell ($IC_{50}$) |
|---|---|---|---|
| PKC-412 | 3.2 | | |
| *203 | 5.8 | 226 | 1.3 |
| 228 | 0.8 | 228 | 0.8 |
| 233 | 1.4 | 235 | 1.6 |
| 237 | 0.5 | 238 | 1.9 |
| 246 | 1.4 | 241 | 0.9 |
| 221 | 2.4 | 240 | 0.5 |

*no compound was described in WO2011053861 and PCT/US2010/056583.

3. Xenograft Model: Pre-Clinical Efficacy Models

In order to test whether the compound of the current invention shows enough in vivo efficacy, they were tested in xenograft mouse model using MV4-11 cancer cell line.

Methods

Compounds of the invention were tested in xenograft mouse model using MV4-11 cell line of FLT3-ITD. All male animals of 6 weeks old Balb/C nude mice were housed in plastic cages (4~6 mice/cage) containing corn cob and maintained in a pathogen-free facility (20~25° C., 30~70% humidity) with a 12 hour light:dark cycle. Tumor model was established by subcutaneous injection with MV4-11 cell suspension. When the average tumor volume reached approximately 400 mm³ (~5 weeks post tumor implantation), the tumor bearing-mice were assigned 2 groups (9 mice per each). The compound 238 treatment of 30 mg/kg every day was initiated and continue for 28 days. The vehicle 20% hydroxyl-β-cyclodextrin was used. Tumor volume was measured twice weekly. Where applicable, percent tumor regression (PTR) for each group will be calculated by the formula:

PTR=100×(tumor volume$_{initial}$−tumor volume$_{final}$)/(tumor volume$_{initial}$).

Results

The representative compound 238 of Formula (I) shows in Table 4 show 74.6% tumor regression only after 4 day treatment and eventually complete tumor regression after 11 days of compound treatment. This result suggests that the representative compound is very potent anti-tumor activity in xenograft mouse model, suggesting that the compound of the present invention is a great therapeutic option for dys-regulated and/or hyperactive FLT3 induced diseases such as AML and ALL.

TABLE 4

| | Means of Tumor Volume (mm³) | | | | | | | | |
|---|---|---|---|---|---|---|---|---|---|
| Day of treatment | 1 | 4 | 7 | 11 | 14 | 17 | 21 | 25 | 28 |
| Vehicle Control | 310.3 | 525.7 | 874.7 | 1341 | 1736 | 2301 | 2764 | 3279 | 3813 |
| 238 30 mg/kg | 312.8 | 79.4 | 27.6 | 0 | 0 | 0 | 0 | 0 | 0 |
| | Percent Tumor Regression (PTR %) | | | | | | | | |
| Day of treatment | 1 | 4 | 7 | 11 | 14 | 17 | 21 | 25 | 28 |
| 238 30 mg/kg | — | 74.6 | 91.2 | 100 | 100 | 100 | 100 | 100 | 100 |

The contents of all patents, patent applications, and publications listed herein are incorporated herein by reference.

While this invention has been particularly shown and described to example embodiments thereof, it will be understood by those skilled in the art that various changes in form and details may be made therein without departing from the scope of the invention encompassed by the appended claims.

The invention claimed is:

1. A compound represented by Formula (I):

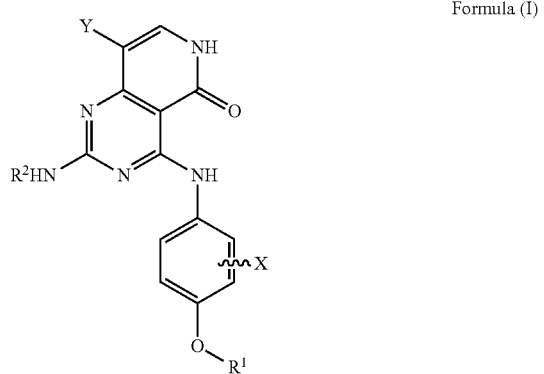

Formula (I)

wherein:
$R^1$ is aryl, arylalkyl, $C_5$-$C_6$cycloalkyl or $C_5$-$C_6$cycloalkyl methyl optionally substituted with $R^3$;
$R^3$ is independently fluoro, chloro, bromo, iodo, $C_1$-$C_6$alkyl, or $CF_3$;
X is F, Cl, Br, I, $CH_3$, or $CF_3$;
Y is chloro, bromo, iodo, —$C_1$-$C_3$alkyl or phenyl;
$R^2$ is $C_4$-$C_7$heterocycloalkyl, wherein the $C_4$-$C_7$heterocycloalkyl has 1 or nitrogen atoms in the $C_4$-$C_7$ heterocycloalkyl ring, and is substituted at nitrogen with $R^5$; and
$R^5$ is $C_1$-$C_3$alkyl or $C(O)C_1$-$C_3$alkyl, wherein the $C_1$-$C_3$alkyl group is optionally substituted with 1-3 fluorine atoms;
or a pharmaceutically acceptable salt thereof.

2. The compound of claim 1, wherein $R^1$ represents phenyl, benzyl, cyclohexyl, cyclopentyl, cyclohexyl methyl, or cyclopentyl methyl optionally substituted with $R^3$.

3. The compound of claim 1, wherein $R^2$ represents piperidine substituted at nitrogen with $R^5$.

4. The compound of claim 1, where $R^5$ is methyl, ethyl, trifluoroethyl, or iso-propyl.

5. The compound of claim 1, wherein the compound is 8-bromo-2-((1-methylpiperidin-4-yl)amino)-4-((4-phenoxyphenyl)amino)pyrido[4,3-d]pyrimidin-5(6H)-one, 8-bromo-4-((4-(3-fluorophenoxy)phenyl)amino)-2-((1-methylpiperidin-4-yl)amino)pyrido[4,3-d]pyrimidin-5(6H)-one or 8-bromo-4-((3-(3-fluorophenoxy)phenyl)amino)-2-((1-methylpiperidin-4-yl)amino)pyrido[4,3-d]pyrimidin-5(6H)-one.

6. The compound of claim 1, wherein Y represents bromo.

7. The compound of claim 1, wherein X represents H, fluorine or methyl.

8. The compound of claim 7, wherein the compound is 8-bromo-4-((3-fluoro-4-phenoxyphenyl)amino)-2-((1-methylpiperidin-4-yl)amino) pyrido[4,3-d]pyrimidin-5(6H)-one hydrochloride.

9. A steroisomeric compound of claim 1.

10. A pharmaceutical formulation comprising a compound or a pharmaceutically acceptable salt thereof of claim 1 in combination with a pharmaceutically acceptable carrier, diluent or excipient.

11. A method of inhibiting FLT3 activity in a cell, the method comprising contacting the cell with an effective amount of a compound or a pharmaceutically acceptable salt thereof of claim 1, such that FLT3 activity is inhibited.

12. A method for the treatment of a hematological malignancy, wherein the hematological malignancy is selected from the group consisting of acute lymphocytic leukemia (ALL), acute myeloid leukemia (AML), chronic lymphocytic leukemia (CLL), chronic myeloid leukemia (CML), and myeloproliferative disorders (MPD), the method comprising administering to a subject in need thereof an effective amount of a compound or a pharmaceutically acceptable salt thereof of claim 1.

13. The method of claim 12, wherein said compound is administered singly or in combination with one or more additional therapeutic agents.

14. The method of claim 12, wherein said compound is administered via intravenous administration, subcutaneous administration, inhalation, oral administration, rectal administration, parenteral, intravitreal administration, intramuscular administration, intranasal administration, dermal administration, topical administration, optic administration, ophthalmic administration, buccal administration, tracheal administration, bronchial administration, or sublingual administration.

* * * * *

UNITED STATES PATENT AND TRADEMARK OFFICE
CERTIFICATE OF CORRECTION

PATENT NO.         : 8,877,763 B2                                                    Page 1 of 1
APPLICATION NO.    : 13/841827
DATED              : November 4, 2014
INVENTOR(S)        : Hong Woo Kim It is certified that error appears in the above-identified patent and that said Letters Patent is hereby corrected as shown below:

In the Claims

Column 34, line 2, Claim 1:

$C_4$-$C_7$ heterocycloalkyl has 1 or nitrogen atoms in the" should be changed to "$C_4$-$C_7$ heterocycloalkyl has 1 or 2 nitrogen atoms in the."

Signed and Sealed this
Eighth Day of September, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,877,763 B2 | Page 1 of 1 |
| APPLICATION NO. | : 13/841827 | |
| DATED | : November 4, 2014 | |
| INVENTOR(S) | : Hong Woo Kim | |

It is certified that error appears in the above-identified patent and that said Letters Patent is hereby corrected as shown below:

Claims

In Claim 1:

At column 33, line number 58, "X is F, Cl, Br, I, $CH_3$, or $CF_3$;" should be corrected to "X is H, F, Cl, Br, I, $CH_3$, or $CF_3$;"

Signed and Sealed this
Sixth Day of December, 2016

Michelle K. Lee
*Director of the United States Patent and Trademark Office*